United States Patent [19]

Hillion et al.

[11] 4,192,960

[45] Mar. 11, 1980

[54] PROCESS FOR MANUFACTURING DICYCLOHEXANOL PROPANE BY HYDROGENATION OF DIPHENOL PROPANE

[75] Inventors: Gérard Hillion, Herblay; Christian Lassau, Villepreux, both of France

[73] Assignee: Institut Francais du Petrole, Rueil Malmaison, France

[21] Appl. No.: 885,223

[22] Filed: Mar. 10, 1978

[30] Foreign Application Priority Data

Mar. 10, 1977 [FR] France .................................. 77 07444

[51] Int. Cl.² ............................................. C07C 35/21
[52] U.S. Cl. .................................................... 568/816
[58] Field of Search .......................................... 568/816

[56] References Cited

U.S. PATENT DOCUMENTS

| 2,118,954 | 5/1938 | Thomas | 568/816 |
| 4,001,343 | 1/1977 | Gaillard et al. | 568/816 |

FOREIGN PATENT DOCUMENTS 45-35300 11/1970 Japan ........................................ 568/816

*Primary Examiner*—Howard T. Mars
*Attorney, Agent, or Firm*—Millen & White

[57] ABSTRACT

Diphenol propane is hydrogenated in the presence of a homogeneous catalyst; water and an alcohol are added at the end of the reaction to assist in the separation of the catalyst residues.

16 Claims, No Drawings

PROCESS FOR MANUFACTURING DICYCLOHEXANOL PROPANE BY HYDROGENATION OF DIPHENOL PROPANE

This invention relates to an improvement in the manufacture of dicyclohexanol propane by hydrogenation of diphenol propane, also named 4,4′-isopropylidene diphenol or Bis-phenol A, by means of molecular hydrogen.

This reaction has been long known as, for example, from U.S. Pat. No. 2,118,954.

Several operating methods are known for performing this hydrogenation. The catalysts are usually noble or non-noble metals from group VIII, for example, platinum, palladium, rhodium, nickel (nickel on a carrier, Raney nickel, etc.) or cobalt. The so-called "homogeneous" catalyst obtained by reacting at least one transition metal compound with at least one metal hydride or organometal compound may also be employed. Solvents such as hydrocarbons, alcohols and ethers have been disclosed.

These methods are operated with a high solvent proportion, about 40% b.w. of solvent with respect to the reactant. The presence of a solvent substantially reduces the productivity of the apparatus and increases the operation constraints (time-consuming and laborious distillation, high partial pressure when using light solvents such as iso-propanol).

When operating without solvent, with a homogeneous catalyst without particular care, there is obtained a highly colored product which contains non-negligible amounts of catalyst residues.

The process of the invention, which avoids the above disadvantages, relates to a process for manufacturing dicyclohexanolpropane by hydrogenation of diphenolpropane by means of molecular hydrogen, in the presence of a homogeneous hydrogenation catalyst consisting of the reaction product of at least one transition metal compound with at least one metal hydride or organometal compound, wherein the reaction is effected without solvent up to the desired degree of hydrogenation, an alcohol and water are added, the catalyst is separated from the resulting alcoholic dicyclohexanolpropane solution, and the latter is fractionated to separately collect the alcohol and dicyclohexanolpropane.

The catalyst is a mixture of (or the reaction product from) at least one transition metal compound, for example at least one nickel, cobalt, iron, titanium and/or molybdenum compound, preferably a nickel compound, with at least one metal hydride or organometal compound, the latter having at least one carbon-metal bond, for example an Al R$_3$ compound where the radicals R are selected from hydrogen, hydrocarbyl and hydrocarbyloxy, at least one being hydrogen or hydrocarbyl.

The operation is conducted at, for example, 140°–240° C., preferably 160°–220° C., these limits being illustrative and not limitative.

Catalysts of this type are disclosed in such documents as the U.S. Pat. Nos. 3,655,799; 3,663,635; 3,784,481 and 3,773,657 or the French Pat. No. 2,228,536 whose disclosures are incorporated herein by way of reference.

The whole catalyst amount may be charged at the beginning of the reaction, or may be supplied by fractions or continuously during the course of the reaction.

According to a preferred alternative embodiment, the catalyst is a homogeneous catalyst obtained from an organoaluminum compound and a mixture of nickel and iron compounds; by the end of the reaction, for example, when the conversion has attained 85 to 97%, an additional amount of nickel and iron compound or of homogeneous iron-free nickel catalyst may be added.

The alcohol and water are added when diphenolpropane has been hydrogenated to the desired degree. The alcohol may however be introduced earlier, for example when 80% or more of the theoretical hydrogen amount has been absorbed, and water is introduced thereafter. Water may also be first introduced, and the alcohol thereafter.

The alcohol is, for example, isopropanol, cyclohexanol or 2-ethylhexanol. The alcohols comprise, for example, 1 to 12 carbon atoms, preferably 3 to 8 carbon atoms, per molecule.

The amount of alcohol may be selected within broad limits; a substantial effect is already obtained, for example, with as low a proportion as 0.05 part by weight of alcohol per part by weight of bis-phenol. There is no upper limit and there could be used, for example, 1 or 2 parts by weight or more of alcohol per part by weight of bis-phenol A. The disadvantage would lie in the larger amount of solvent to be distilled off.

The amount of water must be sufficient to make the catalyst insoluble in the alcoholic medium; it must not be excessive to avoid the separation of the solvent from the hydrogenation product. The amount of water is usually at least 0.005 part b.w., preferably 0.01 to 0.1 part b.w. per part b.w. of bis-phenol A.

The filtration temperature is usually in the range from 120° to 220° C., these limits being not obligatory.

Hydrogen may be pure or diluted with inert gases.

The following examples illustrate the invention but are not limitative thereof:

EXAMPLE 1

A catalyst previously prepared by reacting 1.4 millimole nickel octoate and 0.35 millimole of iron octoate with 5.6 millimole of triethylaluminum in 10 ml of heptane, is added to 200 g of molten diphenolpropane.

After 4 hours reaction at 210° C. under 30 bars hydrogen, hydrogen is no more absorbed (the amount absorbed at this time is approximately the theoretical amount) and the temperature of the reactor is decreased to 200° C. 15 ml water and 20 ml 2-ethyl-1-hexanol are then added and the contents are discharged. The catalyst is separated by filtration, 2-ethyl-1-hexanol is distilled and there is collected a perfectly clear, uncolored distillation residue containing 99% dicyclohexanolpropane. The metal content (nickel+iron) is lower than 0.5 ppm by weight.

EXAMPLE 2 (comparison)

Example 1 is repeated, except that only 15 ml water and no alcohol is added at the end of the reaction. After separation of the catalyst, strongly colored dicyclohexanolpropane is collected. The metal content is about 10 ppm by weight.

When using 35 ml water, instead of 15 ml, the above disadvantage is yet present.

EXAMPLE 3

Example 1 is repeated, while using 20 ml of cyclohexanol instead of 2-ethyl-1-hexanol. After separation of the catalyst, the product is slightly colored. This shows that 2-ethyl-1-hexanol is a better solvent than cyclohexanol.

EXAMPLE 4

Example 1 is repeated, but 2-ethyl-1-hexanol is replaced by the same volume of isopropyl alcohol. After separation of the catalyst, the product appears as practically uncolored.

EXAMPLE 5 (comparison)

Example 1 is repeated, except that 35 ml 2-ethyl-1-hexanol and no water is added at the end of the reaction. The catalyst, which does not precipitate, cannot be separated by filtration.

What we claim is:

1. In a process for producing a dicyclohexanolpropane by hydrogenation of diphenolpropane, which comprises the steps of contacting diphenolpropane with molecular hydrogen in the presence of a homogeneous hydrogenation catalyst consisting essentially of the reaction product of at least one transition metal compound with a compound of the formula $AlR_3$, where each radical R is selected from hydrogen, hydrocarbyl and hydrocarbyloxy, at least one being hydrogen or hydrocarbyl, thereby forming dicyclohexanolpropane; and recovering the resultant dicyclohexanolpropane, the improvement of which comprises:
   (a) effecting the catalytic hydrogenation to form dicyclohexanolpropane in the absence of a solvent for the diphenolpropane until at least 80% of the theoretical amount of hydrogen has been absorbed; and only then
   (b) adding at least 0.05 part by weight of an alcohol having 1–12 carbon atoms and at least 0.005 part by weight of water for each part by weight of starting diphenolpropane, thereby forming (1) a solution of the alcohol and dicyclohexanolpropane and (2) an insoluble catalyst phase; wherein the amount of water added is sufficient to effect the formation of an insoluble catalyst phase but insufficient to cause separation of the alcohol from the solution of alcohol and dicyclohexanolpropane;
   (c) separating the catalyst phase from the solution of alcohol and dicyclohexanolpropane; and
   (d) recovering dicyclohexanolpropane from the separated solution of the alcohol and dicyclohexanolpropane.

2. A process according to claim 1, wherein said transition metal compound is at least one nickel, cobalt, iron, titanium or molybdenum compound.

3. A process according to claim 1, wherein said step (a) is continued until the absorption of hydrogen ceases.

4. A process according to claim 1, wherein the recovery of dicyclyhexanolpropane as a residue in step (d) is effected by fractional distillation of the alcohol.

5. A process according to claim 1, wherein the separation of the catalyst phase in step (c) is effected by filtration at a temperature of 120°–220° C.

6. A process according to claim 1, wherein the hydrogenation step (a) is effected at a temperature of 140°–240° C.

7. A process according to claim 3, wherein said nickel compound is nickel octoate and said iron compound is iron octoate.

8. A process according to claim 1, wherein said $AlR_3$ is triethylaluminum.

9. A process according to claim 7, wherein said $AlR_3$ is triethylaluminum.

10. A process according to claim 1, wherein the metal of said transition metal compound is a group VIII noble metal.

11. A process according to claim 1, wherein the metal of said transition metal compound is nickel.

12. A process according to claim 1, wherein said transition metal compound is a mixture of a nickel compound and an iron compound.

13. A process according to claim 1, wherein in step (b) the alcohol is added in an amount of 0.05–1 part by weight per part by weight of starting diphenolpropane.

14. A process according to claim 1, wherein the alcohol comprises 3–8 carbon atoms per molecule.

15. A process according to claim 1, wherein the alcohol is 2-ethyl-1-hexanol.

16. A process according to claim 1, wherein in step (b) the amount of water added is 0.01–0.1 part by weight per part by weight of starting diphenolpropane.

* * * * *